United States Patent
Moussouni et al.

(10) Patent No.: US 9,498,652 B2
(45) Date of Patent: Nov. 22, 2016

(54) COMPOSITION, PROCESS FOR PREPARATION AND METHOD OF USE

(75) Inventors: Farid Moussouni, Montvale, NJ (US); Delphine Son, Hull (GB); Anne Tindal, Hull (GB)

(73) Assignee: RECKITT BENCKISER (UK) LIMITED, Berkshire (GB)

( * ) Notice: Subject to any disclaimer, the term of this patent is extended or adjusted under 35 U.S.C. 154(b) by 462 days.

(21) Appl. No.: 12/087,703

(22) PCT Filed: Jan. 15, 2007

(86) PCT No.: PCT/GB2007/000087
§ 371 (c)(1),
(2), (4) Date: Sep. 26, 2008

(87) PCT Pub. No.: WO2007/080411
PCT Pub. Date: Jul. 19, 2007

(65) Prior Publication Data
US 2009/0049619 A1    Feb. 26, 2009

(30) Foreign Application Priority Data

Jan. 16, 2006    (GB) .................................. 0600788.4

(51) Int. Cl.
*A61Q 9/04*    (2006.01)
*A61K 8/81*    (2006.01)
*A61K 8/04*    (2006.01)
*A61K 8/34*    (2006.01)

(52) U.S. Cl.
CPC ................. *A61Q 9/04* (2013.01); *A61K 8/044* (2013.01); *A61K 8/342* (2013.01); *A61K 8/8182* (2013.01)

(58) Field of Classification Search
USPC ........................................... 424/400; 8/94.16
See application file for complete search history.

(56) References Cited

U.S. PATENT DOCUMENTS

| | | | |
|---|---|---|---|
| 3,865,546 A * | 2/1975 | Zemlin et al. | ..................... 8/161 |
| 5,716,602 A * | 2/1998 | Uick | ................................ 424/59 |
| 6,203,784 B1 * | 3/2001 | Martin et al. | ................... 424/73 |
| 6,479,043 B1 | 11/2002 | Tietjen et al. | |
| 2004/0170586 A1 * | 9/2004 | Ferrari et al. | ................... 424/63 |
| 2008/0213205 A1 * | 9/2008 | Moussouni | ................. 424/70.1 |

FOREIGN PATENT DOCUMENTS

| | | | |
|---|---|---|---|
| FR | 2631825 A1 * | 12/1989 | |
| GB | 2 367 749 A | 4/2002 | |
| WO | WO 99/02125 | 1/1999 | |
| WO | WO 2004100910 A1 * | 11/2004 | |
| WO | WO 2005/096880 A | 10/2005 | |
| WO | WO 2006/021782 A | 3/2006 | |
| WO | WO 2007/080411 A1 | 7/2007 | |

OTHER PUBLICATIONS

Ashland, Sun Care Technologies, retrieved online on May 19, 2014.*
SciFinder, VP/Hexadecene Copolymer, retrieved online on May 19, 2014.*
PCT International Search Report, PCT/GB2007/000087, dated Apr. 26, 2007.
Combined Search and Examination Report under Sections 17 and 18(3) dated May 31, 2006.
Written Opinion of the International Searching Authority, PCT/GB2007/000087.

* cited by examiner

*Primary Examiner* — Jennifer Berrios
(74) *Attorney, Agent, or Firm* — Troutman Sanders LLP; Ryan A. Schneider; Chris N. Davis

(57) ABSTRACT

Depilatory compositions comprising a depilatory agent, fatty alcohol and VP/hexadecene copolymer provide improved resistance to rinsing of the compositions from the skin. The compositions provide for a method-of depilation in wet conditions using a tool to apply and remove the compositions.

9 Claims, 1 Drawing Sheet

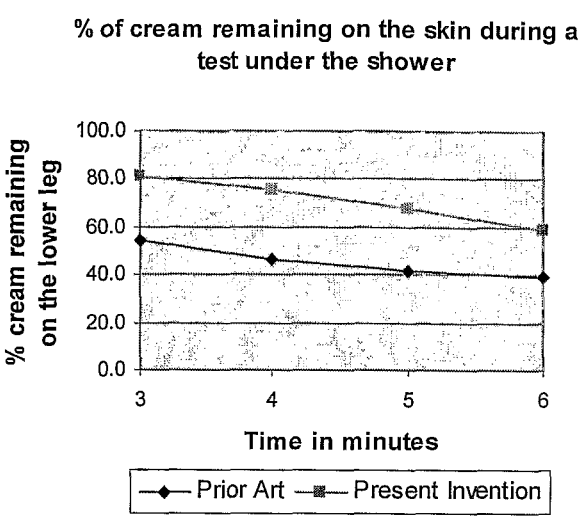

COMPOSITION, PROCESS FOR PREPARATION AND METHOD OF USE

The present invention relates to depilatory compositions in the form of an oil-in-water emulsion; their preparation, and methods for their use in removing hair from the skin of humans.

Compositions for removing superfluous body hair are known and are of various types. One type of composition requires initial heating before being applied to the skin in a generally molten state. It is then allowed to solidify before being removed from the skin together with unwanted hair. This is known in the art as epilation, as the hairs are uprooted from the skin.

Another type of composition is in the form of a cream, which can be applied to the skin at room temperature. The cream includes a substance that degrades hair keratin. Conventionally, the compositions are applied to the skin where unwanted hair is present, then left in place for a predetermined time to allow the keratin in the hair to become degraded. The composition along with degraded hair is then removed from the skin, usually with a tool such as a sponge or wipe or spatula. Such compositions are known in the art as depilatory compositions.

If the depilatory composition is left in contact with the skin for excessive lengths of time, there is a risk that the composition may cause irritation of the skin in some users. If it is present for too short a time, degradation of keratin may be inadequate, leading to only partial removal of the unwanted hair. In this specification, the period the composition must be left in contact with the hairy skin to achieve adequate hair degradation is referred to as the degradation period. Typical degradation periods are in the range 3 to 15 minutes.

In the art, the trend has been to make depilatory compositions sufficiently viscous so that they will stay in place on desired region of skin where superfluous hair removal is desired, without slipping to other regions of skin or falling off during the degradation period. In parallel, there has also been a trend to make the compositions easier to rinse from the skin, so that once the degradation period is over, the composition and degraded hairs can be rinsed easily from the skin. See for example EP0855900.

WO 99/02125 discloses depilatory compositions in the form of oil-in-water emulsions. The preferred depilatory compound is cited as potassium thioglycolate. A pH regulator is present, the preferred pH regulator being lime (calcium hydroxide).

A problem with prior art depilatory compositions arises from their ease of rinsing. The user generally applies the compositions in the bathroom by a bathtub, sink or shower, or even in a bath or shower, and must wait for several minutes before removing the composition, but is prevented from simultaneously carrying out any other procedures which could lead to the composition being inadvertently rinsed away or partially rinsed away. This would potentially lead to patches of hair remaining on the skin. So, for instance, with prior art compositions, the user would be inhibited from applying the composition to their legs then washing their upper body, or shampooing their hair, or shaving their armpits during the degradation period. This can lead to a considerable lengthening of the total time required for ablutions when removal of superfluous hair is desired.

It has now been found that these problems can be tackled by providing a depilatory composition which remains in place on the skin for enough time for hair degradation to take place even when rinsed or immersed in water for short periods of time.

BRIEF DESCRIPTION OF THE DRAWING

FIG. 1 is a graph of an experimental result for the present invention.

In a first aspect, the invention provides a depilatory composition which is an emulsion of hydrophobic particles in a continuous aqueous phase wherein the aqueous phase comprises at least one depilatory agent and the hydrophobic particles comprise a fatty alcohol and a VP hexadecene copolymer.

Surprisingly, the presence of the VP hexadecene copolymer along with the fatty alcohol in the hydrophobic particles of the composition leads to a considerable improvement in the adherence of the composition to the skin even when subjected to a stream of rinsing water. It is surprising that the VP hexadecene copolymer, which is located in the discrete, hydrophobic particles of the composition, has such an influence on the rinse-ability of the compositions.

In a second aspect, the invention provides a method of hair removal from human skin which includes the steps of
i) applying a composition according to the first aspect of the invention to the skin where superfluous hair is present,
ii) allowing the composition to remain in contact with the skin for a predetermined time, and iii) removing the composition and degraded hair.

Preferably, a removal tool is used to remove the composition and degraded hair.

Further aspects of the invention are concerned with processes for preparing the depilatory compositions and their use for degrading hair keratin in a wet environment, where there is risk of accidental rinsing away of the composition, such as a bathroom.

A particularly preferred hexadecene copolymer is a VP/hexadecene copolymer preferably having a molecular weight from about 4000 to 13,000, such as 5000 to 11,000, mass units. A particularly preferred molecular weight is in the range 6,500 to 8,500, such as about 7,300. Such a copolymer provides the advantage of ease of incorporation of the hexadecene into the hydrophobic particles of the invention by melting and blending. A VP hexadecene suitable for use in compositions of the invention is a polymer with the structure $(C_{22}H_{41}NO)_x$.

The depilatory agent is a substance capable of degrading keratin. The depilatory agent, according to the present invention, may include a mixture of one or more depilatory agents. Preferred depilatory agents are sulfhydryl compounds, meaning a compound having an —S—H group. Suitable sulfhydryl depilatory agents include but are not limited to the group consisting of thioglycolic acid, cysteine, homocysteine, glutathione, thioglycerol, thiomalic acid, 2-mercaptopropionic acid, 3-mercaptopropionic acid, thiodiglycol, 2-mercaptoethanol, dithiothreitol, thioxanthene, thiosalicylic acid, thiolactic acid, thiopropionic acid, thiodiglycolic acid, N-acetyl-L-cysteine, lipoic acid, and cosmetically- and/or pharmaceutically acceptable salts of any of the foregoing compounds.

Preferred sulfhydryl compounds include thioglycolic acid, cysteine, glutathione, N-acetyl-L-cysteine, lipoic acid, thiosalicylic acid, and thiolactic acid and cosmetically- and/or pharmaceutically-acceptable salts thereof More preferred sulfhydryl compounds include thioglycolic acid, cysteine, glutathione and N-acetyl-L-cysteine and cosmeticallyand/or pharmaceutically acceptable salts thereof. The most preferred sulfhydryl compound is thioglycolic acid and cosmetically- and/or pharmaceutically-acceptable salts thereof. As used herein, "cosmetically- and/or pharmaceutically-acceptable salts" of the sulfhydryl compounds include, but are not limited to alkali metal salts, e.g., sodium, lithium, rubidium and potassium salts; alkaline earth metal salts, e.g., magnesium, calcium and strontium salts; non-toxic heavy metal salts, e.g., aluminum salts and zinc salts; boron salts; silicon salts; ammonium salts; trialkylammonium salts, e.g., trimethylammonium and triethylammonium; and tetralkylonium salts.

Preferred cosmetically- and/or pharmaceutically-acceptable salts of the sulfhydryl compound include sodium, potassium and calcium salts. Most preferred salts of the sulfhydryl compound are potassium and calcium salts.

Suitably, the composition comprises from 1 to 8% by weight, preferably from 2 to 6% by weight, of depilatory agent expressed as the acid form of the depilatory agent. For example, it is preferred that the composition comprises potassium glycolate at pH12.3, this is not expressed as potassium thioglycolate, but as the equivalent weight of thioglycolic acid.

Optionally, the composition includes an accelerator that will accelerate the keratin degradation reaction. Suitable accelerators include urea, thiourea, dimethyl isosorbide, ethoxydiglycol and methyl propyl diol. Preferably the accelerator is urea or methyl propyl diol. The composition according to the invention preferably comprises from 5% to 15% by weight, more preferably 7% to 10% by weight of an accelerator.

It is particularly preferred for the composition to comprise a pH regulator to assist in activating the depilatory agent, particularly when the depilatory agent is a sulfhydryl compound. Preferably the quantity and type of pH regulator is chosen to maintain the pH of the composition at a value greater than 5, preferably greater than 7, more preferably from 8 to 13, most preferably from 10 to 12.9, especially from 12 to 12.7.

For example, by ensuring that the pH is about 12.1 to 12.7, depilation can occur within about 5 minutes, as desired by the user, without causing undue irritation. Higher pH levels can lead to irritation problems with some users.

The pH regulator preferably is in the continuous aqueous phase (between the hydrophobic particles) when present. Examples of the pH regulator include arginine (especially L-arginine), silicates (e.g. sodium or potassium silicate), calcium hydroxide and polyethyleneimine. Mixtures of pH regulators may be used. It is particularly preferred for the pH regulator also to include calcium hydroxide in an amount from 2 to 4% by weight of the composition. The pH regulator may be dissolved in the aqueous phase of the composition or may be present as solid particles dispersed throughout the composition.

Compositions according to the invention comprise hydrophobic particles distributed as an emulsion (an oil-in-water emulsion) in an aqueous continuous phase which is a liquid at 25° C. By aqueous it is meant that the continuous phase comprises at least 50% by weight of water, preferably 70% by weight or more based on the total weight of the continuous phase. The amount of water in the composition as a whole will typically be from 40% to 95% by weight of the composition.

The hydrophobic particles of the compositions of the invention may comprise non-polar oily or waxy materials which are insoluble in water (by insoluble is meant a solubility in water of 0.1% by weight or less at 25° C.) but must comprise a fatty alcohol. Preferably, the alkyl/alkenyl chain of the fatty material is fully saturated. Suitable fatty alcohols comprise from 8 to 22 carbon atoms, more preferably 16 to 22. A mixture of fatty alcohols may also be used. Preferred fatty alcohols include cetyl alcohol, stearyl alcohol and mixtures thereof.

Suitably, the amount of fatty alcohol in compositions of the invention is 3% or more, preferably 5% or more, most preferably 7% or more by weight of the composition. Suitably, compositions of the invention comprise less than 20%, preferably less than 15%, more preferably less than 11% by weight of fatty alcohol.

The hydrophobic particles of the composition further comprise an oil gelling agent. Suitable oil gelling agents include waxes having a melting point from 65° C. to 130° C., polymeric gelling agents and mixtures thereof. Compositions of the invention suitably comprise from 0.2 to 5%, preferably from 0.5 to 4% more preferably from 1 to 3% by weight of the oil gelling agent.

Suitable waxes include beeswax, carnauba, baysberry, candelilla, montan, ozokerite, ceresin, hydrogenated castor oil (castor wax), synthetic waxes such as Fisher-Tropsch waxes, microcrystalline waxes, and mixtures thereof. Waxes such as triglycerides or glycol diesters of $C_{18}$ to $C_{36}$ fatty acids are also suitable as gelling agent for the oil phase.

Particles means finely divided parts, and encompasses solid particles, liquid particles and plastic or waxy particles. Preferably, the particles are solid at a temperature of 25° C. or less. Preferably, the particles are liquid at a temperature of 80° C. or more in order to facilitate the preparation of the composition. The hydrophobic particles suitably have a mean diameter $D_{4,3}$ as measured by laser light scattering (using apparatus such as a Malvern Mastersizer™) from 0.1 to 50 micrometers, preferably from 0.5 to 20 micrometers, more preferably from 1 to 10 micrometers.

Preferably, compositions of the invention include an emulsifier to facilitate the emulsification of the hydrophobic particles in the continuous aqueous phase and to stabilise the emulsion against coalescence of the hydrophobic particles. In general the emulsifier is an anionic, cationic, non-ionic or zwitterionic surfactant. Preferably the emulsifier is a non-ionic surfactant. Suitable nonionic surfactants include alkyl ethers of polyethylene glycol and/or polypropylene glycol, including mixed ethers and mixtures thereof. The emulsifier is suitably present in an amount of from 2% to 10%, most preferably from 3% to 8% by weight of the composition.

The compositions of the invention, in addition to the hydrophobic particles and the aqueous continuous liquid phase, may also include other ingredients that are conventionally present in depilatory formulations, such as perfumes, oils, and pigments (such as titanium dioxide) and thickeners such as a clay.

Suitable clays for thickening may include organophilic and layered clay minerals belonging to the geological classes of the smectites, the kaolins, the illites, the chlorites, the attapulgites and the mixed layer clays. Typical examples of specific clays belonging to these classes are: 1) smectites, e.g. montmorillonite, bentonite, pyrophyllite, hectorite, saponite, sauconite, nontronite, talc, beidellite; 2) illites, e.g., bravaisite, muscovite, paragonite, phlogopite; 3) chlorites, e.g., corrensite, penninite, donbassite, sudoite; 4) attapulgites, e.g., sepiolite, and polygorskyte.

The layered clay minerals may be either naturally occurring or synthetic. Preferred clay minerals for use in the present invention are natural or synthetic smectites and attapulgites, (particularly the hectorites, montmorillonites and bentonites,) and of these the hectorites are especially preferred. Many of the above clays are available commercially, and typical examples of commercial hectorites are the Laponites ex Laporte Industries Ltd., England; Veegum Pro and Veegum F ex R. T. Vanderbilt, USA; and the Barasyms, Macaloids and Propaloids ex Baroid Division, National Lead Company, USA. If a clay is used for thickening, it is preferably in an amount of from 0.1 to 10% by weight, more preferably from 0.1 to 1% by weight of the composition.

The inclusion of a clay, preferably sodium lithium magnesium silicate, is particularly advantageous, since this provides lithium, sodium and magnesium ions for the buffer system and improves the efficiency of depilation. It is particularly preferred if the clay is a synthetic hectorite clay such as Laponite™.

Other optional water-soluble thickening agents which may be used include Carbomer™ (Acrylic acid polymer, preferably cross-linked), acrylic polymer emulsions (e.g. acrylate/steareth-20 methracylate copolymer), polysaccharides, cellulose based thickeners or natural thickeners such as gum arabic, alginates, carrageenan, locust bean gum, xanthan gum and polyvinyl alcohol. Mixtures of thickeners may be used.

A suitable method for preparing compositions according to the invention comprises the following steps:
1) Blending the fatty alcohol, emulsifier and oil gelling agent together into a molten phase at a temperature of 60, preferably 70° C. or more,
2) emulsifying the molten phase into an aqueous phase, the temperature of the aqueous phase prior to emulsification being 50° C., preferably 60° C., more preferably 70° C. or more, whereby an emulsion comprising dispersed hydrophobic particles is formed,
3) cooling the emulsion to a temperature of 40° C. or less,
4) dispersing the depilatory agent and any accelerator in the emulsion.

The depilatory agent and any optional accelerator is preferably not added until after the emulsion has been cooled to prevent degradation of the depilatory agent (which may occur at substantially elevated temperatures). Any optional ingredients may be added thereafter; however it is preferred for any clay to be added at an elevated temperature.

In an alternative process according to the invention, the temperature of the aqueous phase may be below 40° C., preferably below 25° C. prior to emulsification whereby the temperature of the resulting emulsion, comprising dispersed particles, has a temperature of 40° C. or less, whereby no further cooling step is required prior to dispersing the depilatory agent and any accelerator in the emulsion. Alternatively, the depilatory agent and any optional accelerator may be present in the aqueous phase prior to the addition of the molten phase to the aqueous phase.

The second aspect of the invention provides a method of hair removal from human skin including the steps of i) applying a composition according to the first aspect of the invention to the skin where superfluous hair is present, ii) allowing the composition to remain in contact with the skin for a predetermined time, iii) removing the composition and degraded hair using a removal tool, and iv) preferably washing the skin, For this second aspect of the invention, it is preferred if the composition is applied to the skin with an application tool, giving the advantage that the composition does not come into contact with the users hands. A block of material such as a sponge or a spatula may be employed, but a preferred application tool is a glove, mitt or thumbless mitt, preferably furnished with an inner layer or membrane which is impermeable to the composition. Preferably, the membrane is also impermeable to water.

The composition and degraded hair are preferably removed from the skin using a removal tool. A block of material such as a sponge or a spatula may be employed, but a preferred application tool is a glove, mitt or thumbless mitt, preferably furnished with an inner layer or membrane which is impermeable to the composition. Preferably, the membrane is also impermeable to water.

It is particularly advantageous if the application tool and removal tool are provided as a combined tool which has two distinct sides, i.e. front and back, which are distinguishable by the user, one side being adapted to apply the composition to the skin, and the other side being adapted to remove the composition from the skin. This has the advantage that only a single combined tool is needed for the application and removal while minimising or preventing contact of the users hands with the composition and preventing accidental transfer of the composition to other parts of the body while ablutions are being performed. Preferably the front and back faces of the tool are of distinctly different texture and/or colour.

Preferably the tool is a mitt or glove, more preferably a thumbless mitt, comprising an inner layer of a first material and an outer layer of a second material with an impermeable layer of flexible polymer membrane sandwiched between the inner and outer layers. Preferably the front and back faces of the tool are of distinctly different texture and/or colour. A thumbless mitt has the advantage that the user can apply the composition with the mitt on one hand, using the application side, then use the same mitt on the same hand for removal, using the removal side.

In an alternative embodiment, the tool may be in the form of a block of material, such as a rectangular parallelipiped or an ellipsoidal shape suitable to be held in the hand.

Preferably the block is formed of two portions which are joined together, wherein one portion is adapted for application of the composition of the invention, and preferably is non-porous, and the other portion is adapted for removal of the composition and degraded hair, and is preferably porous and more preferably spongy and is even more preferably furnished with a textured surface suitable for massaging or exfoliating the skin. Preferably the portion adapted for application of the composition is substantially impermeable to water and to the composition.

Therefore, according to yet a further aspect of the present invention, there is provided a depilatory tool having a first side arranged to apply a depilatory composition, and a second side arranged to remove a depilatory composition, wherein the first side and the second side are substantially of a different texture and/or colour.

Advantageously, the first side and/or the second side are in of cellular material such as a foam or sponge-like material. The sponge may be a natural sponge or a synthetic sponge. It is envisaged that the second side is more coarse or abrasive then the first side thereby assisting in the removal of the depilatory cream together with the degraded hair.

According to the invention there is further provided the use of a composition according to the invention to degrade hair keratin.

Throughout this specification, percentages of ingredients by weight are referenced to the weight of the total composition, unless otherwise specified. The following Examples illustrate the invention.

A composition was prepared according to the formulation given in table 1 by emulsifying a melt at 70° C. formed from the cetearyl alcohol, cetearyl 20, ppg-15 stearyl ether paraffin wax and VP hexadecene copolymer. The resulting blend was cooled to 40° C. prior to addition of the depilatory agent: other ingredients were blended while cooling from 70 to 40° C.

The resultant composition was applied to an area of skin having superfluous hair thereon, a prior art depilatory formulation was applied to a similar sized area of skin having superfluous hair thereon. The % of depilatory cream left on the skin after 3, 4, 5 and 6 minutes under a stream of water from a shower head is given in the form of a graph in FIG. 1s, wherein the graph represents the % of cream remaining on the skin during the test.

The resultant compositon demonstrated improved reduced rinsability when compared to prior art depilatory compositions.

TABLE 1

| Ingredient | %( ) |
| --- | --- |
| Ceteareth 20 (Emulgin B2) | 3.0 |
| Cetearyl Alcohol 30/70 | 8.0 |
| PPG - 15 Stearyl Ether (Arlamol E) | 2.55 |
| VP/Hexadecene copolymer | 1.9 |
| Paraffin wax | 5.2 |
| Urea | 7.5 |
| Ca Hydroxide | 4.00 |
| Na Gluconate | 0.1 |
| Mg Trisilicate | 0.75 |
| Premix pink Paste | 0.5 |
| Lotus flower milk | 0.15 |
| Acrylate copolymers | 0.15 |
| Potassium thioglycolate premix | 12.0 |
| Thelma 200 | 0.6 |
| Spray dried silica | 0.05 |
| KOH 50% solution | 1 |
| Deionised Water | 52.55 |

The invention claimed is:

1. A depilatory composition comprising an emulsion of hydrophobic particles in a continuous aqueous phase, wherein
   the continuous aqueous phase comprises a depilatory agent,
   the hydrophobic particles consist of a fatty alcohol and a vinylpyrrolidone/hexadecene copolymer,
   the depilatory agent is a sulfhydryl compound, and
   the inclusion of a vinylpyrrolidone/hexadecene copolymer and a fatty alcohol in a hydrophobic particle provide adherence qualities of the composition to hairy skin such that the composition has a degradation period greater than three minutes, wherein the degradation period is the time the composition is left in contact with hairy skin to achieve adequate hair degradation even when rinsed or immersed in water,
   the vinylpyrrolidone/hexadecane copolymer is in an amount of about 1.9% by weight of the total composition,
   the vinylpyrrolidone/hexadecane copolymer has a molecular weight in the range of 6,500 to 8,500 mass units, and
   the vinylpyrrolidone/hexadecane copolymer is a polymer with the structure $(C_{22}H_{41}NO)_x$.

2. A depilatory composition according to claim 1, comprising from 3 to 20% by weight of fatty alcohol.

3. A depilatory composition according to claim 2, wherein the fatty alcohol has an alkyl chain comprising from 8 to 22 carbon atoms.

4. A depilatory composition according to claim 1, comprising from 1 to 8% by weight of depilatory agent, expressed as the equivalent acid form of the depilatory agent.

5. A kit for hair removal comprising:
   a depilatory tool, and
   the depilatory composition of claim 1;
      wherein the depilatory tool comprises a first side arranged to apply a depilatory composition, and a second side arranged to remove a depilatory composition, wherein the first side and the second side are substantially of a different texture and/or colour.

6. The kit of claim 5, wherein the depilatory composition comprises from 3 to 20% by weight of fatty alcohol and wherein the fatty alcohol has an alkyl chain having from 16 to 22 carbon atoms.

7. The kit of claim 5, wherein the depilatory agent comprises a cosmetically acceptable salt of thioglycolic acid and the depilatory agent comprises from 1 to 8%, by weight of the depilatory composition, expressed as an equivalent acid form of the depilatory agent.

8. A depilatory composition comprising an emulsion of hydrophobic particles in a continuous aqueous phase, wherein:
   the continuous aqueous phase comprises a depilatory agent,
   the hydrophobic particles consist of a fatty alcohol and hexadecene copolymer,
   the depilatory agent is a sulfhydryl compound, and
   the inclusion of a hexadecene copolymer and a fatty alcohol in a hydrophobic particle provide adherence qualities of the composition to an applied surface such that over 60% of the composition remains on a surface when subjected to three minutes of running water.

9. The depilatory composition of claim 8, wherein the inclusion of a hexadecene copolymer and a fatty alcohol in a hydrophobic particle provide adherence qualities of the composition to an applied surface such that over 60% of the composition remains on a surface when subjected to five minutes of running water.

* * * * *